United States Patent [19]
Tipping et al.

[11] Patent Number: 5,824,660
[45] Date of Patent: Oct. 20, 1998

[54] METHOD OF INHIBITING GLOMERULONEPHRITIS

[75] Inventors: Peter G. Tipping, Clayton, Australia; Tze-Chein Wun, St. Louis, Mo.

[73] Assignee: G. D. Searle & Co., Chicago, Ill.

[21] Appl. No.: 661,236

[22] Filed: Jun. 10, 1996

[51] Int. Cl.$^6$ .......................... A61K 31/725; A61K 38/00
[52] U.S. Cl. .................................................. 514/56; 514/2
[58] Field of Search ............................................ 514/2, 56

[56] References Cited

U.S. PATENT DOCUMENTS

| | | | |
|---|---|---|---|
| 4,966,852 | 10/1990 | Wun et al. | 435/235 |
| 5,106,833 | 4/1992 | Broze et al. | 514/12 |
| 5,212,091 | 5/1993 | Diaz-Collier et al. | 435/69.6 |
| 5,276,015 | 1/1994 | Khouri et al. | 514/12 |
| 5,466,783 | 11/1995 | Wun et al. | 530/380 |

OTHER PUBLICATIONS

Broze, Semin, Hematol. 29, 159–169 (1992).
Rapaport, Blood 73, 359–365 (1989).
Broze et al; Blood 71: 335–343 (1988).
Sandset et al; Proc. Natl. Acad. Sci. USA 88, 708–712 (1991).
Sandset et al; Thromb. Res. 50, 803–813 (1988).
Novotny et al; Blood 78, 387–393 (1991).
Sandset et al; Blood 78, 1496–1502 (1991).
Day et al; Blood 76, 1538–1545 (1990).
Creasey et al; J. Clin. Invest. 91, 2850–2856 (1993).
Werling et al; Thromb. Haemost. 69, 366–369 (1993).
Diaz–Collier et al; Thromb. Haemost. 71, 339–346 (1994).
Broze et al; Biochemistry 29, 7539–46 (1990).
Broze, Annu. Rev. Med. 46, 103–112 (1995).
Wun, Blood 79, 430–438 (1992).
Morita et al. *Jpn. J. Nephrol.* 1991, 36(7), 832–838.
Jesty et al. *Biochemistry* 1994, 33, 12686–12694.

*Primary Examiner*—Kathleen K. Fonda
*Attorney, Agent, or Firm*—Scott J. Meyer

[57] ABSTRACT

There is disclosed a method of inhibiting fibrin dependent glomerulonephritis which comprises administering to a warm-blooded mammal a heparin/TFPI complex which consists of a weight ratio of at least 1.25 parts of heparin to one part of TFPI.

5 Claims, 8 Drawing Sheets

FIG. 1A
FIG. 1B
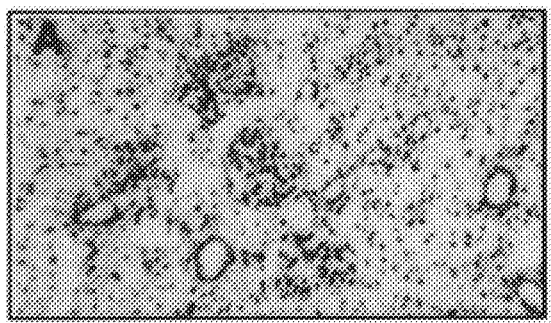
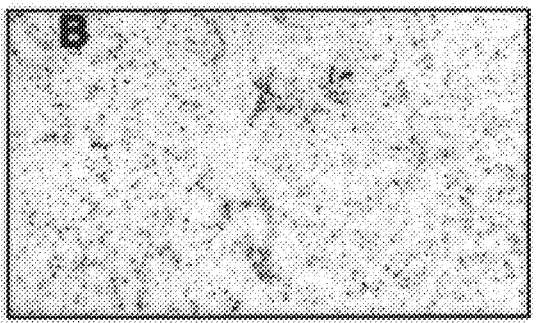
FIG. 1C
FIG. 1D
FIG. 1E
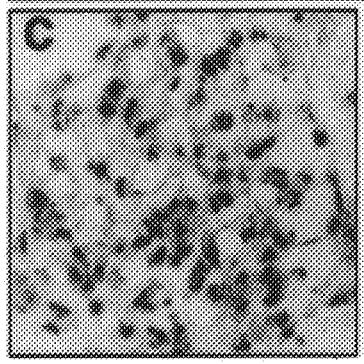
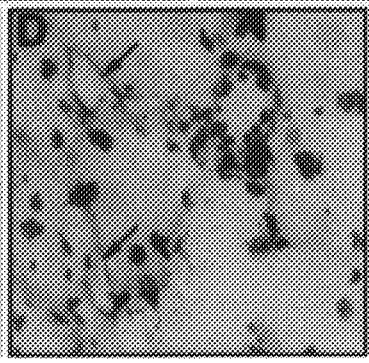

FIG. 1F
FIG. 1G
FIG. 1H
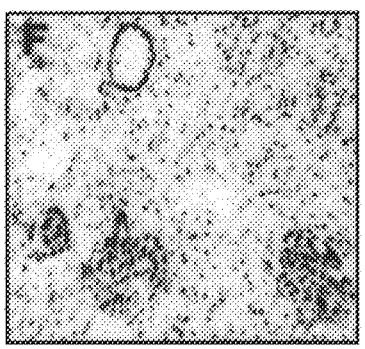
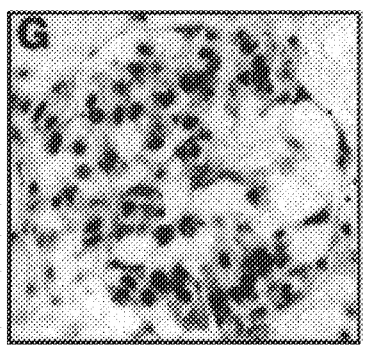
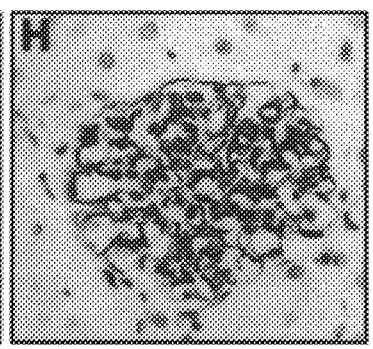
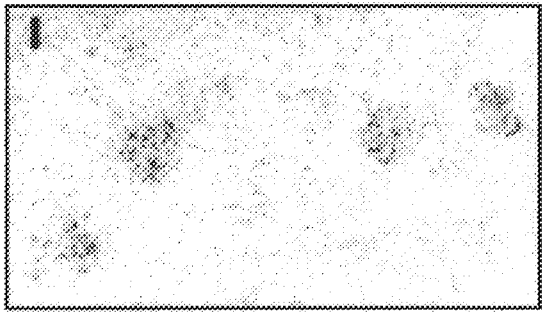
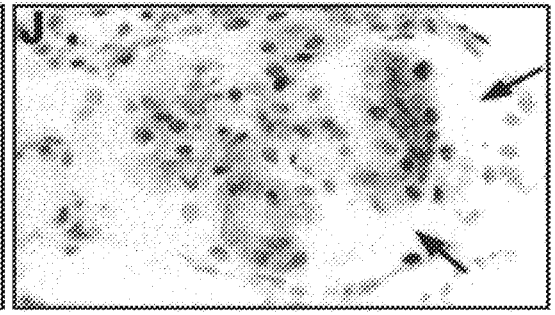
FIG. 1I
FIG. 1J

METHOD OF INHIBITING GLOMERULONEPHRITIS

BACKGROUND OF THE INVENTION

The present invention relates to a method of inhibiting glomerulonephritis and, more particularly, to inhibition of fibrin-dependent glomerulonephritis by administration of heparin/TFPI complexes.

(Note: Literature references on the following background information and on the conventional test methods and laboratory procedures well known to the ordinary person skilled in the relevant art and other such state-of-the-art techniques as used herein are indicated in parentheses and appended at the end of the specification.)

Tissue factor pathway inhibitor (TFPI) is the naturally occurring inhibitor of tissue factor (TF), the major in vivo activator of the coagulation cascade (1,2). TFPI is thought to inhibit TF/VIIa activity in a two-step reaction. First, TFPI binds and inhibits factor Xa, then the TFPI/Xa complex binds to TF/VIIa resulting in inhibition of TF/VIIa activity (3,4).

In man, TFPI exists free in the circulation and also in association with lipoproteins and in platelets. The major pool of TFPI is on the surface of endothelial cells (1,5). In rabbits, TFPI is not lipoprotein bound and plasma TFPI has a molecular weight between 43 and 45 kD (6,7). TFPI bound to endothelial cells may play a critical role in controlling factor Xa generation and coagulation at sites of local endothelial cell injury.

TFPI synthesis by endothelial cells in vitro does not appear to be regulated by proinflammatory cytokines such as interleukin 1 (IL-1) and tumor necrosis factor $\alpha$ (TNF$\alpha$) (8), which regulate TF and plasminogen activator inhibitor-1 (PAI-1) production.

In vivo, in both man and rabbits, TFPI on endothelial cells is released from glycosaminoglycan binding sites by heparin (9,10), however few factors which regulate the synthesis of TFPI have been identified. Evidence for a functional role for TFPI in vivo has been provided by experimental studies.

In rabbits, immunological inhibition of TFPI results in sensitization to the effects of systematically administered tissue factor (TF) (6) and endotoxin (11). When administered at pharmacological doses, in short term models, TFPI inhibits thromboplastin-induced intravascular coagulation (12) and reduces mortality from endotoxemia in baboons (13).

The renal expression of TFPI has not been fully characterized. A single previous report described TFPI expression limited to the microvasculature of the renal cortex (14). The expression of TFPI in glomeruli and its regulation in vivo are undefined heretofore.

BRIEF DESCRIPTION OF THE INVENTION

In accordance with the invention, a method is provided for inhibiting fibrin dependent glomerulonephritis in a warm-blooded mammal. The method comprises exogenous administration to a warm-blooded mammal of an inhibitory effective amount of a pre-formed heparin/TFPI complex. The active complex consists of a weight ratio of at least 1.25 parts of heparin to one part of TFPI. Administration of the heparin/TFPI complex provides a significant reduction in glomerular fibrin deposition (GFD), proteinuria and renal impairment which is not obtained by separate administration of either heparin or TFPI.

A preferred range of the weight ratio of the active complex is from 1.25 to about 100 parts of heparin to one part of TFPI.

The pre-formed heparin/TFPI complex can be conveniently prepared by simple admixture of the heparin and TFPI in the above-stated weight ratio in physiologically acceptable buffer solution, e.g., normal physiologic saline (0.15M NaCl, pH 7.4). Preferably, the TFPI is dissolved in a buffer that permits high solubility of $\geq 5$ mg/ml, e.g., (A) 2M urea-saline, (B) 0.2M L-arginine-20 mM phosphate-saline, or (C) 5% mannitol-0.1 mM HCl), and the heparin is dissolved in saline. The respective TFPI and heparin solutions are then mixed to form soluble heparin/TFPI complexes and the mixture diluted in saline solution.

The glomerulus is a high flow vascular bed which is vulnerable to injury by fibrin (15, 16). This is particularly evident in rapidly progressive crescentic forms of glomerulonephritis (GN), where defibrination has been demonstrated to provide significant protection from injury (17, 18).

As described herein, an investigation was made of the glomerular expression of TFPI in kidneys of normal rabbits and in a crescentic model of fibrin dependent GN. In the normal kidneys, TFPI was expressed in glomeruli, in intrarenal arteries and in interstitial capillary network. In the crescentic model of GN, fibrin is the key mediator of injury.

In these tests of glomerulonephritis, it was unexpectedly found that administration of the heparin/TFPI complex significantly ameliorated local fibrin deposition resulting from trauma or inflammation.

DETAILED DESCRIPTION OF THE INVENTION

While the specification concludes with claims particularly pointing out and distinctly claiming the subject matter regarded as forming the present invention, it is believed that the invention will be better understood from the following detailed description of preferred embodiments of the invention taken in conjunction with the appended drawings in which:

BRIEF DESCRIPTION OF THE DRAWINGS

FIG. 1, in ten parts, A–J, shows: Photomicrographs demonstrating the distribution of TFPI antigen in kidneys by immunoperoxidase staining with a monoclonal anti-rabbit TFPI antibody (FIG. 1A to FIG. 1E).

Staining in a normal kidney demonstrates TFPI expression in glomeruli and intrarenal vessels, but not on parietal aspect of Bowman's capsule or in tubules (FIG. 1A, magnification ×100).

No staining is observed using an irrelevant monoclonal antibody (FIG. 1B, magnification ×100).

At higher magnification, diffuse staining of the glomerular tuft is seen in normal glomeruli in a pattern suggesting endothelial cell expression (FIG. 1C, magnification ×400, compared with FIG. 1F and FIG. 1G).

TFPI is expressed on microvascular endothelium (arrowed) in the renal interstitium (FIG. 1D, magnification ×400) and on the endothelium (arrowed) and adventitia (arrowed) of intrarenal arteries (FIG. 1E, magnification ×400).

The staining pattern using a specific monoclonal anti-rabbit endothelial cell antibody (EC-1) shows a similar staining pattern to TFPI, both at low power (FIG. 1F, magnification ×100) and in the glomerulus at higher magnification (FIG. 1G, magnification ×400).

Glomerular staining with a specific marker of rabbit podocytes (GLEPP-1) shows a quite dissimilar staining pattern to TFPI (FIG. 1H, magnification ×350).

Glomerular TFPI expression is down regulated 24 hours after initiation of antiGBM GN (FIG. 1I, magnification ×100).

Four days after induction of GN, glomerular TFPI is expressed at a similarly intensity to normal and is diffusely distributed throughout the glomerular tuft but not in Bowman's space or on Bowman's capsule (FIG. 1J, magnification ×400).

Figure 2:
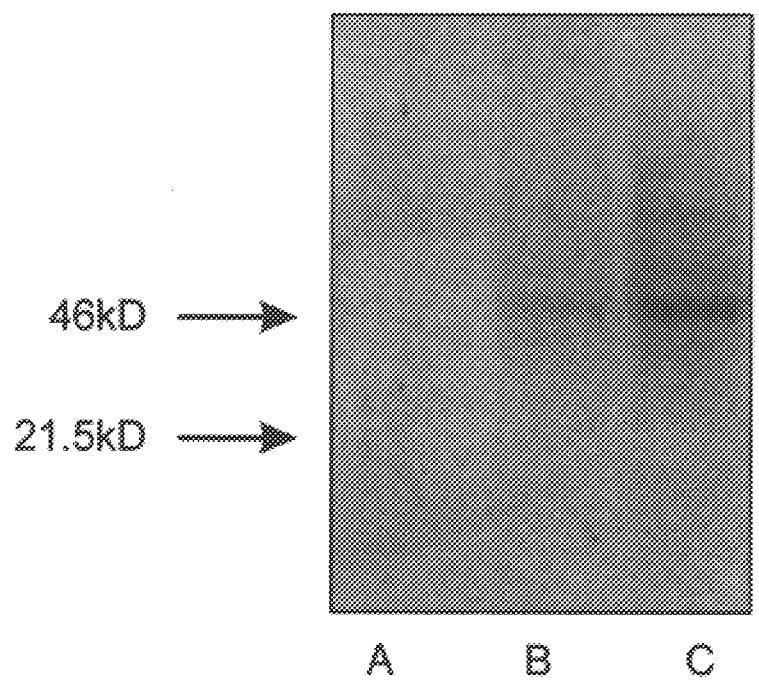

FIG. 2 shows: Immunoaffinity purified, biosynthetically $^{35}S$ labeled TFPI produced by isolated normal glomeruli in vitro, detected by scanning on a Fuji Bio-Imaging BAS®1000 instrument. Labeling is not detectable at 1 hour (Lane A), is barely detectable at 3 hours (Lane B), and is prominent at 18 hours (Lane C).

Figure 3A:
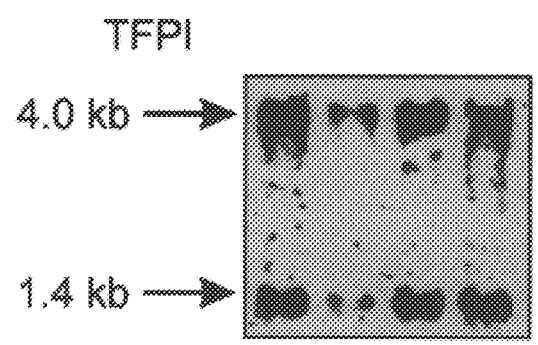
Figure 3B:
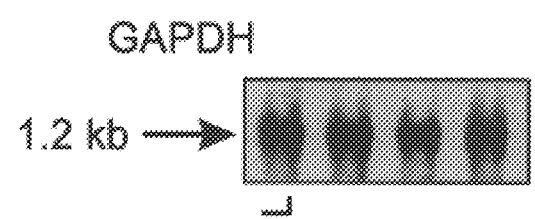

FIG. 3, in two parts, A and B, shows: Northern analysis of poly A+ mRNA from normal rabbit glomeruli and glomeruli from rabbits developing anti-GBM GN on day 1, day 4, and day 7, demonstrating expression of two species (1.2 and 4 kb) of TFPI mRNA (FIG. 3A, upper panel) and GAPDH mRNA (FIG. 3B, lower panel).

Figures 4A, 4B, 4C, 4D:
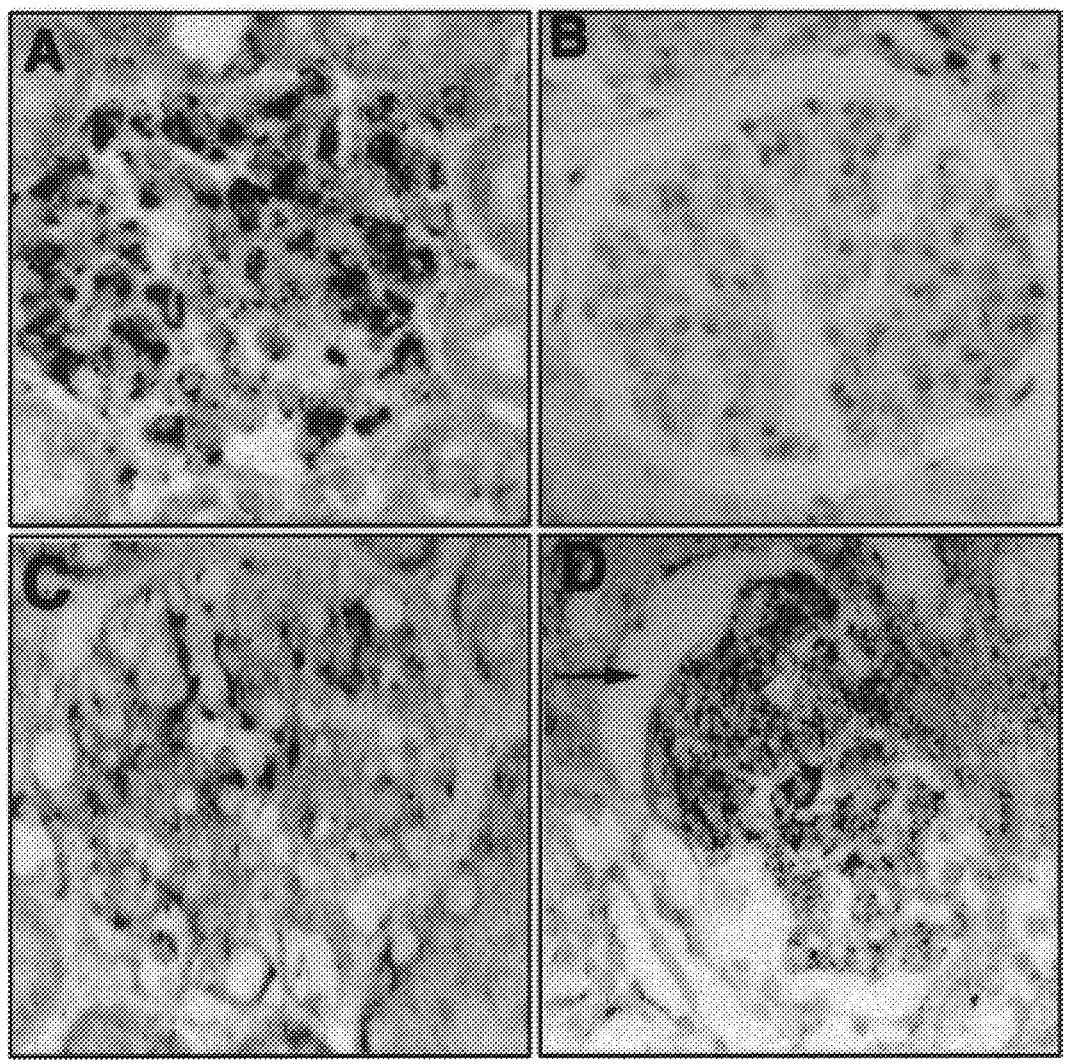

FIG. 4, in four parts, A, B, C and D, shows: Photomicrographs of rabbit glomeruli demonstrating TFPI mRNA by in situ hybridization using a digoxigenin (Dig) labeled probe and alkaline phosphatase reporter system. A strong signal for TFPI mRNA was detected in normal glomeruli with an anti-sense cRNA probe (FIG. 4A) compared to a sense cRNA probe (FIG. 4B).

TFPI mRNA was down regulated 24 hours after initiation of anti-GBM GN (FIG. 4C). However, after 4 days, the pattern and intensity of TFPI mRNA expression was similar to that of normal glomeruli (FIG. 4D). (magnification ×400 in all panels, FIGS. 4A–4D).

FIG. 5, in four parts, A–D, shows: Histological appearances of glomeruli from anti-TFPI antibody and control rabbits with anti-GBM GN.

Figure 5A:
Figure 5B:
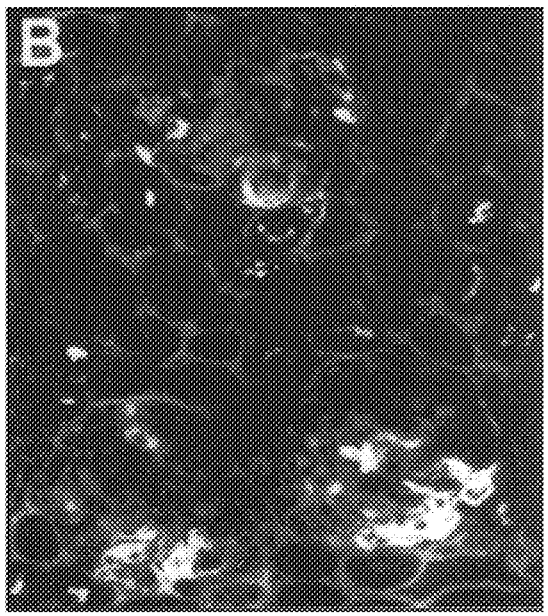
Figure 5C:
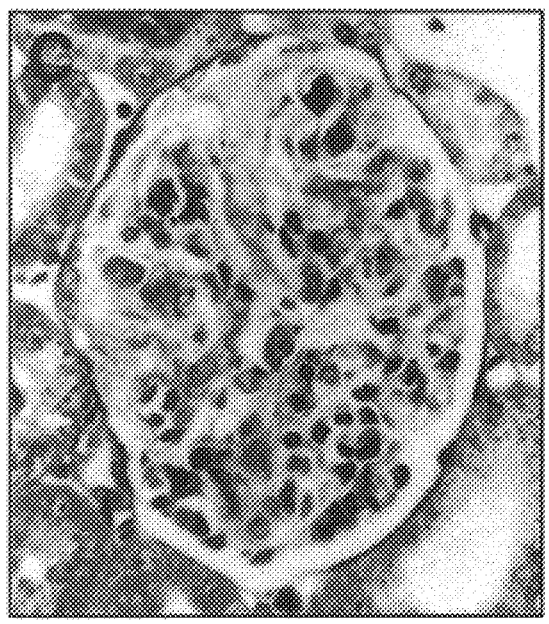
Figure 5D:
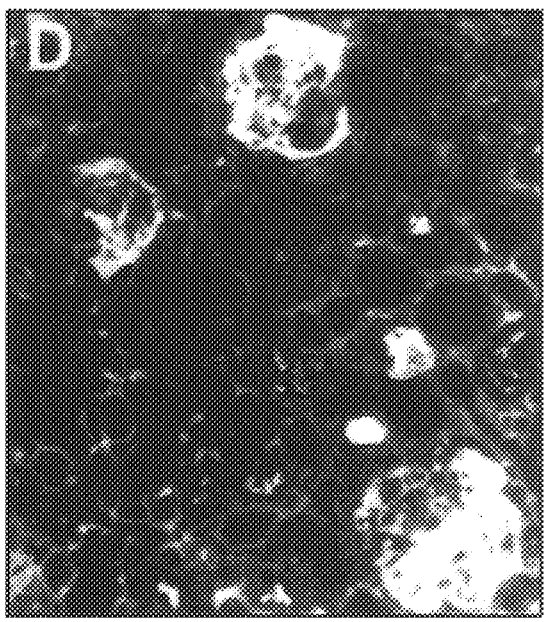

Two days after initiation of GN, rabbits treated with anti-TFPI antibody developed more severe crescentic GN (FIG. 5A) and more prominent fibrin deposition (FIG. 5B) than rabbits treated with normal sheep globulin (FIG. 5C and FIG. 5D).

Figure 6:
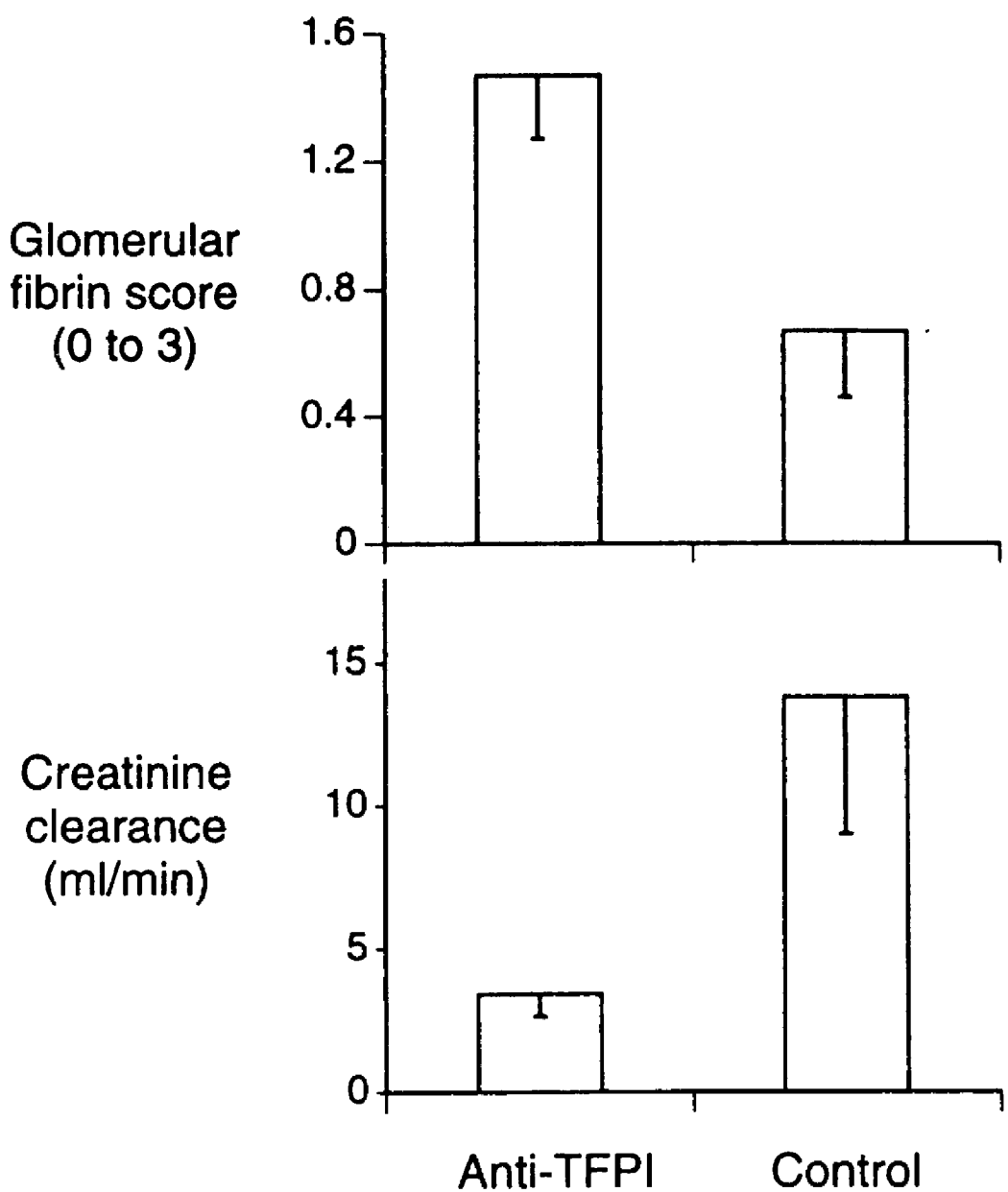

FIG. 6 is a bar graph which shows: Effect of treatment with anti-TFPI antibody in rabbits developing anti-GBM GN.

Top Panel: Glomerular fibrin deposition in the same rabbits assessed by immunostaining of renal cortical sections and scored on a scale from 0 (normal) to 3 (fibrin covering >⅔ of the glomerular cross-section). Fibrin deposition was significantly increased in rabbits treated with anti-TFPI antibody (P<0.05).

Bottom Panel: Creatinine clearance in rabbits developing anti-GBM GN treated with anti-TFPI antibody or control antibody were significantly different P<0.04).

Figure 7:
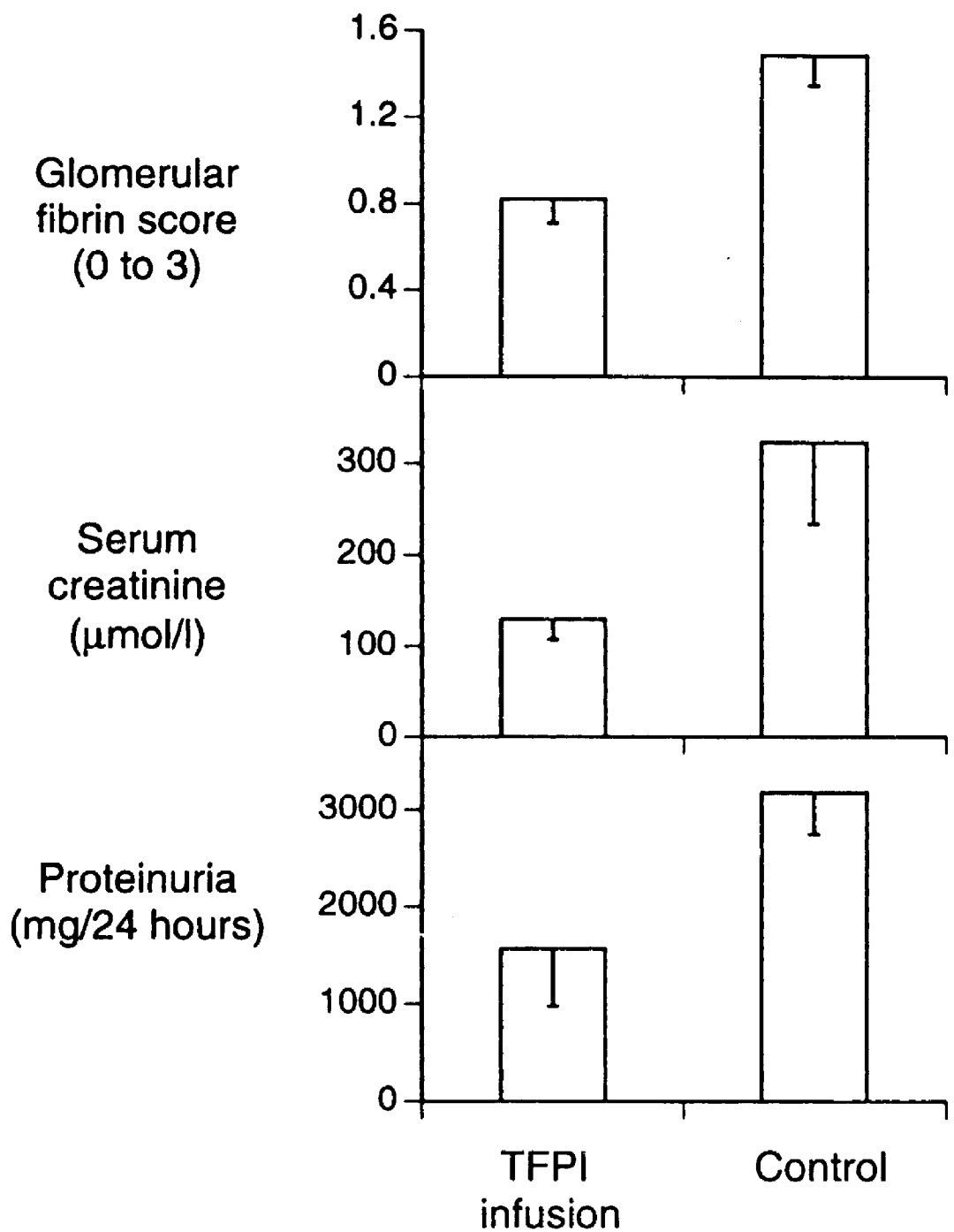

FIG. 7 is a bar graph which shows: Effect of infusion of human recombinant TFPI in the form of heparin/TFPI complex on the development of anti-GBM GN. TFPI-infused rabbits showed a significant reduction of glomerular fibrin deposition (P<0.01), protection of renal function (significant lower serum creatinines, P<0.05) and significantly less proteinuria (P<0.05) when compared with rabbits receiving control infusions.

FIG. 8, in four parts, A–D, shows: Histological appearances of glomeruli from recombinant TFPI treated and control rabbits with anti-GBM GN.

Figure 8A:
Figure 8B:
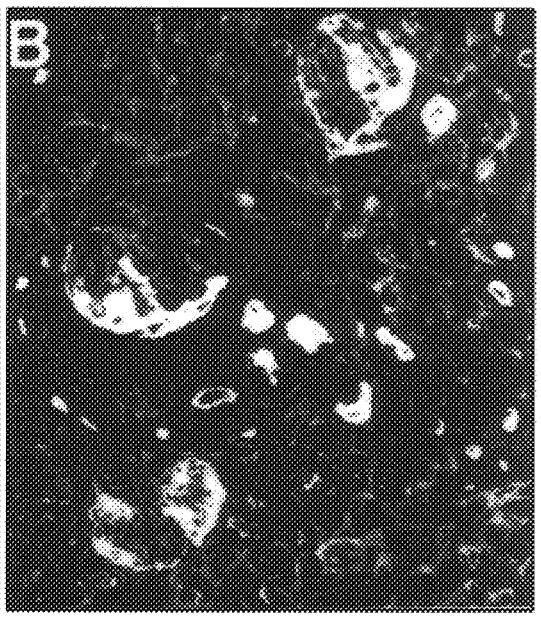
Figure 8C:
Figure 8D:
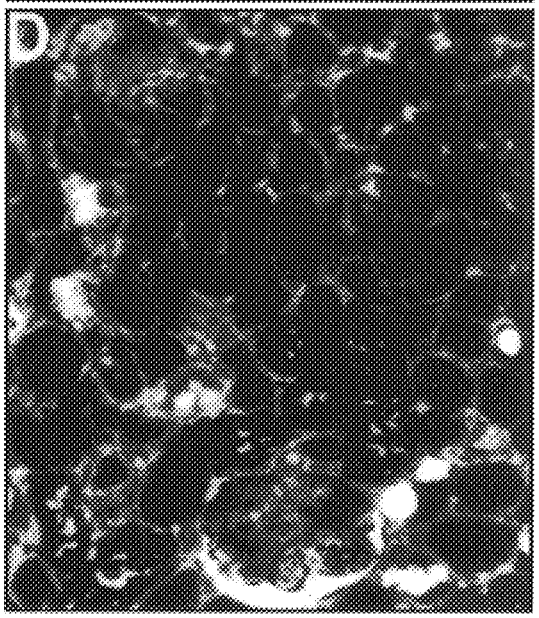

Three days after initiation of GN, rabbits infused with recombinant TFPI showed less severe crescent formation (FIG. 8A) and less fibrin deposition (FIG. 8B) than rabbits receiving control infusions (FIG. 8C and FIG. 8D).

In order to illustrate the invention in greater detail, the following exemplary laboratory preparative work and detailed Examples were carried out. It will be appreciated, however, that the invention is not limited to these specific Examples which are provided for purposes of illustration and not limitation.

EXAMPLES

Methods

Animals.

Male New Zealand White rabbits weighing 1.8 to 2.5 kg were obtained from Monash University Central Animal Services, Clayton, Victoria, Australia.

Production of Polyclonal and Monoclonal Antibodies to Rabbit TFPI.

Recombinant rabbit TFPI was produced by expression of rabbit TFPI cDNA in *E. coli*, refolding and ion-exchange chromatography using the same protocol as that described for the production of recombinant human TFPI (19).

The recombinant rabbit protein was used to raise monoclonal and polyclonal antibodies to rabbit TFPI. A polyclonal antibody was raised in a sheep by immunization with 50 μg of recombinant TFPI in Freund's complete adjuvant (Commonwealth Serum Laboratories [CSL], Parkville, Victoria, Australia, and 5 subsequent boosts of 25 μg of recombinant TFPI in Freund's incomplete adjuvant (CSL).

Sheep plasma was absorbed against rabbit red blood cells and a globulin fraction was prepared by ammonium sulphate precipitation and dialyzed against phosphate buffered saline (PBS).

The antibody was a potent inhibitor of rabbit TFPI in a two-stage chromogenic assay for TFPI activity and recognized a 45 kD protein in rabbit plasma on Western blotting. This corresponds to the previously reported molecular weight of rabbit plasma TFPI (6). This antibody was subsequently used in a TFPI ELISA and for in vivo inhibition.

To raise monoclonal antibodies, Balb/c mice were immunized with 10 μg of purified TFPI in Freund's complete adjuvant and their spleen cells were fused with NS1 cells to produce hybridomas by standard techniques. Supernatants from clones were screened for TFPI reactivity using recombinant antigen coated on microtitre plates. The monoclonality of reactive clones was ensured by subcloning at limiting dilution on two occasions. A number of monoclonal antibodies were produced which stained a 45 kD protein in rabbit plasma and in conditioned medium from rabbit aortic endothelial cells. One clone, which produced an IgG1 antibody, which inhibited TFPI activity in a functional two-stage chromogenic assay (6), was used in an ELISA and for subsequent immunohistochemical studies.

Demonstration of TFPI Antigen by Immunoperoxidase.

Four (4) μm sections of snap frozen renal cortex were fixed for 30 seconds in 70% ethanol and stained with monoclonal anti-TFPI antibody (20 μg/ml). Glomerular endothelial cells were demonstrated using a specific monoclonal anti-rabbit endothelial cell antibody (EC-1, a gift of Dr. S. Kloth, Regensburg, Germany) (20), on cryostat-cut, acetone fixed tissue sections.

Glomerular visceral epithelial cells (podocytes) were demonstrated using a monoclonal antibody to rabbit GLEPP-1, a specific marker of podocytes (provided by Dr. R. Wiggins, Ann Arbor, Mich.) (21), on 2 μm formalin fixed, paraffin embedded tissue sections. Irrelevant isotype matched monoclonal antibodies at identical dilutions were used to assess non-specific staining. A peroxidase antiperoxidase technique, previously used on kidney tissue (21), was employed to detect the primary antibodies.

Demonstration of TFPI Production in vitro.

Glomerular TFPI production in vitro was demonstrated by immunoprecipitation of biosynthetically labeled protein in conditioned medium from cultured normal glomeruli. Renal cortical tissue was collected aseptically and glomeruli isolated by graded sieving as previously described (23).

Isolated glomeruli were washed once in PBS and then in methionine and cysteine free RPMI 1640 medium (ICN Biomedicals Inc., Costa Mesa, Calif., USA) and then cultured at $5\times10^3$/ml in cysteine and methionine free RPMI 1640 with 0.25 mCi of $^{35}$S labeled methionine and cysteine (Amersham, Sydney, Australia).

Culture supernatants were sampled at 1, 3 and 18 hours and subsequently immunoprecipitated using polyclonal anti-rabbit recombinant TFPI or normal sheep globulin bound to Affi-Gel® 15 affinity support (Biorad, Richmond, Calif., USA).

Bound proteins were eluted by boiling the beads in SDS sample buffer containing 50 mM dithiothreitol (DTT) (BioRad) and were then subjected to SDS PAGE and were then transferred onto nitrocellulose. Blots were scanned in a Fuji Bio-Imaging BAS®1000 instrument.

Measurement of TFPI Antigen in Glomerular Lysates and Plasma.

TFPI antigen was measured in a sandwich ELISA using a monoclonal capture antibody and a polyclonal detecting antibody. Monoclonal anti-rabbit TFPI antibody was bound to polyvinyl chloride microtitre plates (Dynatech, Chantilly Va., USA) at a concentration of 4 $\mu$g/ml in 0.1M bicarbonate buffer, pH 9.5 at 4° C., overnight. Plates were blocked with 3% non fat milk powder in PBS and washed twice with PBS.

Glomerular lysates were incubated in a final concentration of 2% Triton® X-100 surfactant and 0.5% bovine serum albumin (BSA) in Tris-saline for 4 hours at 4° C. The samples were spun at 2000 g for 5 minutes and 100 $\mu$l of the supernatant diluted to a final concentration of 1% Triton X-100, 0.5% BSA in Tris-saline and varying concentrations of rabbit recombinant TFPI standard were incubated in wells, overnight at 4° C.

Plates were washed three times in PBS with 0.1% Tween® 20 surfactant (PBST) and then incubated with 100 $\mu$l of sheep anti-rabbit TFPI serum (5 $\mu$g/ml) in PBST containing 0.5% BSA and 1% non fat milk powder for 2 hours at room temperature.

After three further washes, horseradish peroxidase conjugated donkey anti-sheep IgG serum (Silenus, Hawthorn, Victoria, Australia) was added to the wells at a dilution of 1 in 4000 and incubated for 1 hour at room temperature. The plates were again washed three times and incubated with 0.1M 2,2'-azino-di-3-ethylbenzthiazoline sulphonate (ABTS, Boehringer Mannheim, Sydney, Australia) in 0.02% $H_2O_2$. After 20 minutes, the absorbance at 405 nm was read in a microtitre plate reader (MR 7000, Dynatech) and the concentrations of the unknowns were calculated by reference to a standard curve. All standards and samples were assayed in duplicate and the sensitivity of the assay for purified TFPI was <100 pg/ml.

The results were expressed as ng/$10^3$ glomeruli. Plasma TFPI samples were assayed at a final dilution of 1 in 50 and the standards for these assays were diluted in a 1 in 50 dilution of human TFPI depleted plasma (American Diagnostica, Greenwich Conn., USA).

Plasma levels of recombinant human TFPI in rabbits receiving TFPI infusions were assayed using a two site ELISA for human TFPI (American Diagnostica). The assay was performed according to the manufacturers instructions with the following modifications: Plasma samples were assayed at a 1 in 100 dilution in Tris buffered saline pH 7.5 containing 1% Triton X-100 to bring the samples into the range of the assay. Standards were diluted in the same buffer.

Analysis of TFPI mRNA.

RNA was isolated from rabbit glomeruli by guanidine thiocyanate/phenol/chloroform extraction as previously described (24), then poly A+ RNA was isolated by using a PolyATract mRNA isolating system (Promega, Madison, Wis., USA). Northern analysis was performed by electrophoresis of RNA (5 $\mu$g per lane) in a 1.2% agarose gel containing formaldehyde and transferred to nitrocellulose.

Slot blot analysis (BioRad) was performed to quantitate TFPI mRNA in individual rabbit glomerular samples by application of RNA samples (5 $\mu$g per slot) to nitrocellulose. Nitrocellulose filters were then baked in a vacuum oven at 80° C. for two hours, then prehybridized at 42° C. This was followed by hybridization at 80° C. with a $^{32}$P-labeled rabbit TFPI cDNA probe, labelled by the "random priming" method (25) then washed as previously described (26).

mRNA levels were quantitated by exposing filters in a phosphoimager (Fuji Bio-Imaging BAS®1000). Expression of GAPDH mRNA was quantitated using a 330 bp cDNA probe. TFPI mRNA levels in glomeruli during the development of GN was expressed as a percentage of the TFPI mRNA in normal glomeruli after correction for equivalent expression of GAPDH mRNA. (GAPDH=glyceraldehyde-3-phosphate dehydrogenase).

In situ Demonstration of TFPI mRNA in Kidney Sections.

In-situ hybridization to demonstrate TFPI mRNA was performed on 5 $\mu$m tissue sections fixed in 3% paraformaldehyde, using digoxigenin (Dig) labelled TFPI cDNA probe. Sections to be hybridized with the Dig labelled probe were pre hybridized for 1 hour at 42° C., then hybridized at 50° C. overnight with a Dig labelled rabbit TFPI cRNA sense and anti-sense probes (made by in-vitro transcription with Dig-11 dUTP). Probes were approximately 500 bp in length. Detection of specific mRNA was accomplished using anti-Dig alkaline phosphatase antibody (Boehringer Mannheim, Mannheim, FRG) at a dilution of 1 in 5000, followed by incubation with nitroblue tetrazolium-X phosphate for 1 hour. Sections were then counterstained with 1% methyl-green.

Preparation of Anti-GBM Globulin and Induction of GN.

Horse anti-rabbit GBM antibody was prepared as previously described (27,28). GN was induced by intravenous administration of horse anti-rabbit GBM globulin (25 mg/kg) to rabbits, presensitized to horse globulin 5 days earlier by subcutaneous injection of horse globulin (4 mg) in Freund's complete adjuvant (CSL). Groups of rabbits killed at 24 hours (day 1, n=13), 96 hours (day 4, n=6) and on day 7 (n=6) after initiation of anti-GBM GN.

Normal rabbits (n=9) were age and sex matched. Tissues were analyzed for expression of TFPI antigen and mRNA as described above. Other indices of injury at these time points in this model, including glomerular crescent formation, fibrin deposition, proteinuria, macrophage infiltration, tissue factor and changes in fibrinolytic activity have been previously extensively characterized in this model (27,28). (GBM=glomerular basement membrane).

In Vivo Inhibition of TFPI in anti-GBM GN.

Sheep anti-rabbit TFPI serum was absorbed twice with rabbit red blood cells (10% by volume) and a globulin fraction was prepared by precipitation with ammonium sulphate at a final concentration of 50%, then extensively dialyzed against PBS. Presensitized rabbits were treated with (40 mg/kg) sheep anti-rabbit TFPI globulin (n=7) or normal sheep globulin prepared in an identical manner (n=7) one hour prior to induction of GN with anti-GBM globulin as detailed above.

Rabbits were then treated with three further doses of anti-rabbit TFPI or normal sheep globulin at 12 hourly intervals. Renal tissue and blood were collected 48 hours after initiation of GN and urine was collected for the preceding 24 hours. Creatinine clearance, glomerular fibrin deposition, and hematological and coagulation parameters were assessed.

In Vivo Infusion of heparin/TFPI Complex.

Human recombinant TFPI in urea excipient buffer was prepared as previously described (29). TFPI was prepared in complexes with heparin to maintain its solubility and functional activity throughout the period of the infusion. TFPI/heparin complexes were formed by adding TFPI (10.0 mg/ml) in urea excipient buffer to porcine mucous heparin sodium (David Bull Laboratories, Melbourne, Victoria, Australia; activity 160 IU/mg) in a ratio of 1 to 1.25 TFPI to heparin by weight. Solution for infusion was prepared freshly every 12 hours by diluting the stock solution with in sterile PBS to a concentration of 700 $\mu$g/ml.

Silastic catheters inserted in the internal jugular veins of rabbits under pentobarbitone anaesthesia, approximately 2 hours prior to the commencement of the test protocol. Thirty minutes prior to receiving a subnephritogenic dose of anti-GBM globulin, rabbits (n=6) received a bolus of heparin (1.25 mg/Kg)/TFPI(1 mg/Kg) complex followed by a constant infusion of heparin/TFPI complex at a rate of 0.6 ml/hour (3.3 $\mu$g/kg/min of TFPI).

Control rabbits (n=6) were infused with excipient buffer/heparin in PBS. Treated and control rabbits thus received a loading dose of 200 IU/kg and a daily infusion of 950 IU/kg/day of heparin. This dose of heparin has previously been shown to have no effect on GFD or renal failure in anti-GBM GN in rabbits (30,31).

Renal tissue and blood were collected 72 hours after initiation of GN and urine was collected for the preceding 24 hours. Serum creatinine, glomerular fibrin deposition, proteinuria and coagulation parameters were assessed. At the end of each infusion rabbits were carefully inspected for any evidence of internal hemorrhage. Particular attention was paid to assessing the wounds at the site of insertion of the silastic catheters.

Serum Creatinine and Creatinine Clearance.

Serum and urine creatinines were measured by the alkaline picric acid method using an autoanalyzer (Cobas Bio, Roche Diagnostics, Basel, Switzerland). Creatinine clearance was calculated from the serum and urine creatinines and the urine volume.

Assessment of Fibrin Deposition by Immunofluorescence.

Six $\mu$m cryostat-cut renal cortical tissue sections were stained with FITC conjugated sheep anti-rabbit fibrinogen antiserum (Research Plus, Bayonne, N.J., USA) at a titre of 1:100 to assess the deposition of fibrinogen related antigens within glomeruli. GFD was assessed in a blinded protocol. Only glomeruli cut in or near the equatorial cross section were included and the extent of immunofluorescence staining in glomeruli scored on a scale from 0 (normal) to +3 (fibrin deposition involving greater than two thirds of the glomerular cross section) as previously described (17, 27, 32). At least 50 glomeruli per animal were scored.

Measurement of Glomerular TF Activity and Hematological Parameters.

TF activity was measured on isolated glomeruli by a one stage prothrombin assay as previously described (33). Lysates were prepared by sonication and assayed at a dilution of 1 in 10 to 1 in 40. Haemoglobin, white cell counts and platelet counts were all performed on blood collected into EDTA on a Coulter STKS analyzer (Coulter Electronics, Miami, Fla., USA). Measurement of the activated partial thromboplastin time (APTT), prothrombin time (PT) and plasma fibrinogen concentrations were performed on citrated blood specimens using a Electra 1000C automatic coagulation timer (Medical Laboratory Automation Inc., Pleasantville, N.Y., USA).

Statistical Analysis.

Results are expressed as mean ±SEM and statistical analysis was performed using a Students unpaired t test for single group comparisons and Fishers LSD test for multiple group comparisons.

Results

TFPI Expression in the Normal Kidney.

TFPI could be demonstrated in glomeruli and vessels of normal rabbit kidneys by immunoperoxidase staining (FIG. 1A). No staining was seen using an irrelevant isotype matched monoclonal antibody (FIG. 1B). In glomeruli, TFPI was expressed in the glomerular tuft (FIG. 1C) in a staining pattern similar to that observed with a specific rabbit endothelial cell marker (EC- 1) (20) (FIG. 1F and FIG. 1G).

The pattern of TFPI expression was different to that of GLEPP-1 a marker of glomerular visceral epithelial cells (22) (FIG. 1H). TFPI was not seen in tubules, but was detectable on the endothelium and adventitia of intrarenal arteries (FIG. 1E) and in the interstitial capillary network (FIG. 1D).

The presence of TFPI in normal glomeruli was confirmed by extraction and quantitation by immunoassay. In lysates of normal glomeruli, the TFPI content was $10.2 \pm 1.2$ ng/$10^3$ glomeruli [gloms] (Table I). In vitro studies confirmed the capacity of glomeruli to synthesize TFPI. Biosynthetic labelling of TFPI released from normal glomeruli was detectable after 3 hours and strongly evident after 18 hours (FIG. 2).

TFPI mRNA with 2 transcripts of 4.0 and 1.4 kb was detected in glomeruli by Northern blotting (FIG. 3). In situ expression of TFPI mRNA was demonstrated in normal glomeruli (FIG. 4A) and in the endothelium and adventitia of intrarenal arteries. Hybridization was not detected using the sense probe (FIG. 4B).

TFPI in Fibrin Dependent GN.

Rabbits with anti-GBM GN developed a severe crescentic pattern of renal injury with prominent glomerular fibrin deposition as previously described (27,28). In this model, crescents developing at 4 days are predominantly fibrinous. Immunohistochemical detection of TFPI demonstrated a decline in glomerular expression 24 hours after initiation of GN (FIG. 1I), with subsequent return to a similar staining intensity to normal by day 4 (FIG. 1J). At this time, TFPI was prominent in mesangial areas, but was not seen within crescents. TFPI expression in the renal vessels did not appear to change substantially during the evolution of GN.

Glomerular TFPI protein levels measured by ELISA showed similar temporal changes to TFPI antigen detectable by immunostaining. TFPI expression decreased 24 hours after initiation of anti-GBM GN ($7.5 \pm 0.7$ ng/$10^3$ glom, P<0.02 compared to normal and subsequently increased at day 4 ($11.2 \pm 0.7$ ng/$10^3$ glom, P=0.002 compared to day 1) and remained at a similar level on day 7($10.2 \pm 1.6$ ng/$10^3$ glom).

Plasma TFPI levels progressively rose throughout the time course studied (Table I). Expression of glomerular TFPI mRNA showed parallel changes to those of TFPI protein with a 32% decrease at day 1, returning to normal levels at day 4 (Table I). In situ hybridization also demonstrated decreased glomerular TFPI mRNA expression at 24 hours (FIG. 4C). At day 4, in situ TFPI mRNA expression was more prominent than day 1 and similar to the levels in normal glomeruli (FIG. 4D). TFPI mRNA expression was not observed within crescents or in tubular cells at this time.

In vivo Inhibition of TFPI in Crescentic Fibrin Dependent GN.

Forty-eight hours after initiation of anti-GBM GN, GFD, crescent formation and renal impairment was present but not severe (FIG. 5A and FIG. 5B). Treatment of rabbits developing GN with sheep anti-rabbit TFPI resulted in a 54±8% decrease in circulating TFPI plasma activity compared to rabbits treated with normal sheep globulin (P<0.005) (Table II).

Anti-TFPI antibody-treated rabbits developed histologically more severe renal injury (FIG. 5C and FIG. 5D), increased GFD (score 1.47±0.20, control 0.67±0.21, P<0.045) and more renal function impairment (creatinine clearance 3.4±0.8 ml/min, control treatment 13.8±4.8 ml/min, P<0.04) than rabbits treated with normal sheep globulin (FIG. 6). Treatment with anti-TFPI antibody also increased glomerular TF activity (anti-TFPI treated, 15.8±6.7 au/$10^3$ gloms, control treatment 5.7±1.1 au/$10^3$ gloms, P<0.04) but had no significant effect on the plasma APTT, PT, fibrinogen, haemoglobin, white cell or platelets concentrations (Table II).

In vivo Infusion of heparin/TFPI complex in Crescentic Fibrin Dependent GN.

Infusion of heparin/recombinant human TFPI complex resulted in a mean plasma recombinant human TFPI of 749±131 ng/ml. Recombinant human TFPI was not detectable in animals receiving control infusions. TFPI infusion resulted in a significant reduction in GFD (score 0.82±0.11, control 1.49±0.14, P<0.01), proteinuria (1561±586 mg/ml, control 3176±432 mg/ml, P<0.05) and less deterioration in renal function (serum creatinine 129±22 μmol/l, control 323±89 μmol/l, P<0.05 (FIG. 7).

Histologically, these rabbits had less severe disease (FIG. 8C) and less glomerular fibrin (FIG. 8D) than rabbits receiving the control infusions (FIG. 8A), which displayed mesangial fibrin deposition and predominantly fibrinous crescents (FIG. 8B).

The APTT's of rabbits receiving heparin/TFPI complexes (36.4±1.84 sec) or control heparin infusion (38.3±4.0 sec) were 2.1 and 2.2 times control values (17.4±0.5 sec) respectively, with no difference between the groups. The prothrombin times of both groups were normal (TFPI 12.4±0.4 sec, control 12.3±1.0 sec). Plasma fibrinogen levels were also not significantly different between the two groups (TFPI 3.5±0.32 mg/ml, control 3.4±0.51 mg/ml) but both were higher than normal rabbits (2.1±0.1 mg/ml).

There was no evidence of bleeding at the site of insertion of the catheters during the infusions and at the end of the test detailed macroscopic inspection of the insertion site and internal organs did not reveal any evidence of antemortem bleeding.

TABLE I

Glomerular TFPI protein and mRNA and plasma TFPI during the development of anti-GBM GN.

|  | Normal | Day 1 | Day 4 | Day 7 |
|---|---|---|---|---|
| *TFPI protein | 11.1 ± 0.7 | 7.5 ± 0.7 | 11.2 ± 0.7 | 10.2 ± 1.6 |

TABLE I-continued

Glomerular TFPI protein and mRNA and plasma TFPI during the development of anti-GBM GN.

|  | Normal | Day 1 | Day 4 | Day 7 |
|---|---|---|---|---|
| (ng/$10^3$ glomeruli) |  |  |  |  |
| #TFPI mRNA (% of normal glomeruli) | 100 ± 5.5 | 68 ± 4.0 | 95 ± 9 | 88 ± 9 |
| †Plasma TFPI (ng/ml) | 239 ± 41 | 397 ± 51 | 671 ± 124 | 881 ± 129 |

*Glomerular TFPI protein levels were measured by ELISA in lysates of glomeruli from normal rabbits and rabbits 1, 4 and 7 days after induction of anti-GBM GN. There is a significant decrease in TFPI expression between normal and day1 (P < 0.02), and a subsequent increase between day1 and day4 (P < 0.002).
Glomerular TFPI mRNA (levels corrected for GAPDH) showed a significant decrease on day1 of anti-GBM GN compared to normal (P < 0.004) and a subsequent increase on day4 (P < 0.02, compared to day1).
†Plasma TFPI protein levels increased significantly from normal to day1 (P < 0.05) and day1 to day4 (P < 0.05)

TABLE II

The effect of in vivo TFPI inhibition on haematological and coagulation parameters in the blood of rabbits developing in anti-GBM GN.

|  | anti-TFPI globulin | normal sheep globulin |
|---|---|---|
| Prothrombin time (s) | 7.8 ± 0.6 | 8.3 ± 0.7 |
| Activated Partial Thromboplastin Time (s) | 17.6 ± 0.8 | 17.7 ± 1.5 |
| Platelet count (×$10^9$/L) | 271 ± 80 | 247 ± 78 |
| White cell count (×$10^9$/L) | 14.2 ± 3 | 10.2 ± 2.5 |
| Haemoglobin (g/L) | 9.8 ± 0.4 | 9.3 ± 0.5 |
| Plasma fibrinogen (g/L) | 3.7 ± 0.5 | 3.5 ± 0.4 |
| *TFPI plasma functional activity (% of normal) | 62 ± 11§ | 136 ± 18 |

*Measured in a two stage chromogenic assay and expressed as a percentage of the activity in normal plasma.
§P < 0.005 compared to rabbits treated with normal sheep globulin The results set forth in Table III, below, support the conclusion that the uncomplexed TFPI is substantially less effective than the heparin/TFPI complex in preventing the anti-GBM induced GN.

TABLE III

The effect of TFPI infusion on the development of anti-GBM GN.

|  | TFPI#1[a] | TFPI#2[a] | Control#1[b] | Control#2[b] |
|---|---|---|---|---|
| Fibrin score (0–3) | 1.82 | 0.93 | 0.99 | 1.07 |
| Serum creatinine (μM) | 832 | 458 | 499 | 487 |
| Proteinuria (mg/24 h) | 238 | 500 | 911 | 814 |
| Plasma TFPI (ng/ml) | 2638 | 2349 | ND | ND |
| Prothrombin time (sec) | 9.4 | 9.5 | 7.5 | 8.6 |
| APTT (sec) | 35 | 33 | 18 | 18 |

[a]Rabbits were infused with a TFPI solution (2.1 mg/ml in control buffer) at a dose of 10 μg kg$^{-1}$ min$^{-1}$ for 3 days.
[b]Rabbits were infused with a control buffer (0.5M urea, 1.7 mM Na—Ac, 9 mM Na-citrate, 3 mM Na—PO$_4$, 0.15M NaCl, pH 7.4) for 3 days.
Conclusion: The results shown in this table indicated that infusion of 10 μg kg$^{-1}$ min$^{-1}$ of TFPI for 3 days did notsignificantly improve the anti-GBM GN over infusion of control buffer.

The administration of the pre-formed heparin/TFPI complexes to a host or patient in need thereof can be carried out by conventional means, preferably in formulations with pharmaceutically acceptable diluents and carriers. The amount of the heparin/TFPI complex which would normally be administered is primarily dependent on the physical characteristics of the host or patient and the severity of the pathological condition.

The amount to be administered must be an effective amount, that is, an amount which is medically beneficial for inhibiting coagulation or for inhibiting fibrin dependent glomerulonephritis, but which does not present toxic effects which overweigh the advantages which accompany its use. The preferable route is oral or parenteral, e.g. intravenously.

Administration of the heparin/TFPI complexes in solution with conventional aqueous diluents, e.g., physiologic saline, is illustrative. Other suitable formulations of the active heparin/TFPI complex in combination with pharmaceutically acceptable diluents and carriers in therapeutic dosage form can be prepared by reference to general texts in the field such as, e.g., *Remington's Pharmaceutical Sciences*, Eighteenth Edition, 1990, Mack Publishing Co., Easton, Pa.

Various other examples will be apparent to the person skilled in the art after reading the present disclosure without departing from the spirit and scope of the invention. It is intended that all such other examples be included within the scope of the appended claims.

REFERENCES

1. Broze, G. J., Jr. 1992. The role of tissue factor pathway inhibitor in a revised coagulation cascade. Semin Hematol. 29:159–169.
2. Rapaport, S. I. 1989. Inhibition of factor VIIa/tissue factor-induced blood coagulation: with particular emphasis upon a factor Xa-dependent inhibitory mechanism. Blood. 73:359–365.
3. Broze, G. J., Jr., L. A. Warren, W. F. Novotny, D. A. Higuchi, J. J. Girard, and J. P. Miletich. 1988. The lipoprotein-associated coagulation inhibitor that inhibits the factor VII-tissue factor complex also inhibits factor Xa: insight into its possible mechanism of action. Blood. 71:335–343.
4. Warn-Cramer, B. J., L. V. Rao, S. L. Maki, and S. I. Rapaport. 1988. Modifications of extrinsic pathway inhibitor (EPI) and factor Xa that affect their ability to interact and to inhibit factor VIIa/tissue factor: evidence for a two-step model of inhibition. Thromb. Haemost. 60:453–456.
5. Sandset, P. M. and U. Abildgaard. 1991. Extrinsic pathway inhibitor—the key to feedback control of blood coagulation initiated by tissue thromboplastin. Haemostasis 21:219–239.
6. Sandset, P. M., B. J. Warn-Cramer, L. V. Rao, S. L. Maki, and S. I. Rapaport. 1991. Depletion of extrinsic pathway inhibitor (EPI) sensitises rabbits to disseminated intravascular coagulation induced with tissue factor: evidence supporting a physiologic role for EPI as a natural anticoagulant. Proc. Natl. Acad. Sci, U.S.A. 88:708–712.
7. Warn-Cramer, B. J., and S. L. Maki. 1992. Purification of tissue factor pathway inhibitor (TFPI) from rabbit plasma and characterisation of its differences from TFPI isolated from human plasma. Thromb Res 67:367–83.
8. Ameri, A., M. N. Kuppuswamy, S. Basu, and S. P. Bajaj. 1992. Expression of tissue factor pathway inhibitor by cultured endothelial cells in response to inflammatory mediators. Blood. 79:3219–3226.
9. Sandset, P. M., U. Abildgaard, and M. L. Larsen. 1988. Heparin induces release of extrinsic coagulation pathway inhibitor (EPI). Thromb. Res 50:803–813.
10. Novotny, W. F., S. G. Brown, J. P. Miletich, D. J. Rader, and G. J. Broze, Jr. 1991. Plasma antigen levels of the lipoprotein-associated coagulation inhibitor in patient samples. Blood. 78:387–393.
11. Sandset, P M., B. J. Warn-Cramer, S. L. Maki, and S. I. Rapaport. 1991. Immunodepletion of extrinsic pathway inhibitor sensitises rabbits to endotoxin-induced intravascular coagulation and the generalised Shwartzman reaction. Blood. 78:1496–1502.
12. Day, K. C., L. C. Hoffman, M. O. Palmier, K. K. Kretzmer, M. D. Huang, E. Y. Pyla, E. Spokas, G. J. Broze, Jr., T. G. Warren, and T-C. Wun. 1990. Recombinant lipoprotein-associated coagulation inhibitor inhibits tissue thromboplastin-induced intravascular coagulation in the rabbit. Blood. 76:1538–1545.
13. Creasey, A. A., A. C. Chang, L. Feigen, T-C. Wun, F. B. Taylor, Jr., and L. B. Hinshaw. 1993. Tissue factor pathway inhibitor reduces mortality from *Escherichia coli* septic shock. J Clin Invest. 91:2850–2856.
14. Werling, R. W., L. R. Zacharski, W. Kisiel, S. P. Bajaj, V. A. Memoli, and S. M. Rousseau. 1993. Distribution of tissue factor pathway inhibitor in normal and malignant human tissues. Thromb. Haemost. 69:366–369.
15. Kincaid-Smith P. 1973. Coagulation and renal disease. Kidney Int. 2:183–190.
16. McCluskey, R. T., P. Vasalli, G. Gallo, and D. S. Baldwin. 1966. An immunofluorescent study of pathogenic mechanisms in glomerular disease. N Engl J Med 274:695–701.
17. Tipping, P. G., N. M. Thomson, and S. R. Holdsworth. 1986. A comparison of fibrinolytic and defibrinating agents in established experimental glomerulonephritis. Brit. J. Exp. Pathol. 67:481–491.
18. Thomson, N. M., J. Moran, I. J. Simpson, and P. K. Peters. 1976. Defibrination with ancrod in nephrotoxic nephritis in rabbits. Kidney Int. 10:343–347.
19. Diaz-Collier, J. A., M. O. Palmier, K. K. Kretzmer, B. F. Bishop, R. G. Combs, M. G. Obukowicz, R. B. Frazier, G. S. Bild, W. D. Joy, S. R. Hill, M. E. Duffin, M. E. Gustafson, K. D. Junger, R. W. Grabner, G. R. Galluppi, and T. -C. Wun. 1994. Refold and characterisation of tissue factor pathway inhibitor exprssed in *Eschericia coli*. Thromb. Haemost. 71:339–346.
20. Kloth, S., A. Schmidbauer, M. Kubitza, H. A. Weich, and W. W. Minuth. 1994. Developing renal microvasculature can be maintained under perfusion culture conditions. Eur J Cell Biol. 63:84–95.
21. Thomas, P. E., B. L. Wharram, M. Goyal, J. E. Wiggins, L. B. Holzman, and R, C. Wiggins. 1994. GLEPP1, a renal glomerular epilthelial cell (podocyte) membrane protein-tyrosine phosphatase. J Biol Chem. 269: 19953–19962.
22. Huang X. R, S. R. Holdsworth, and P. G. Tipping. 1994. Evidence to a role for delayed type hypersensitivity in glomerular crescent formation. Kidney Int. 46: 69–78.
23. Holdsworth, S. R., Thomson N. M., Glasgow E. F., Dowling J. P., Atkins R. C. 1978. Tissue culture of isolated glomeruli in experimental glomerulonephritis. J Exp Med 147:98–109.
24. Chomczynski, P., and N. Sacchi. 1987. Single step method of RNA isolation by acid guanidinium thiocyanate-phenol-chloroform extraction. Anal. Biochem. 162:156–159.
25. Feinburg, A. P., and B. Vogelstein. 1983. A technique for radiolabeling DNA restriction endonuclease fragments to high specific activity. Anal Biochem. 132: 6–13.

26. Apostolopoulos, J., G. J. Howlett, and N. Fidge. 1987. Effects of dietary cholesterol and hypothyroidism on rat apolipoprotein metabolism. J Lipid Res. 28:642–648.
27. Malliaros J., S. R. Holdsworth, J. Wojta, J. H. Erlich, and P. G. Tipping. 1994. Glomerular fibrinolytic activity in anti-GBM glomerulonephritis in rabbits. Kidney Int. 44: 557–564.
28. Tipping, P. G., J. Erlich, J. Apostolopoulos, N. Mackman, D. Loskutoff, and S. R. Holdsworth. 1994. Glomerular tissue factor antigen, activity and mRNA in crescentic glomerulonephritis. Am J Pathol. 147:1736–1748.
29. Diaz-Collier, J. A., M. O. Palmier, K. K. Kretzmer, B. F. Bishop, R. G. Combs, M. G. Obukowicz, R. B. Frazier, G. S. Bild, W. D. Joy, S. R. Hill, K. L. Duffin, M. E. Gustafson, K. D. Juger, R. W. Grabner, G. R. Galluppi, and T-C. Wun. 1994. Refold and characterisation of recombinant tissue factor pathway inhibitor expressed in *Escherishia coli*. Thromb Haemost. 71:339–346.
30. Thomson, N. M., I. J. Simpson, and D. K. Peters. 1975. A quantitative evaluation of anticoagulants in experimental nephrotoxic nephritis. Clin Exp Immunol. 19: 301–308.
31. Border, W. A., C. B. Wilson, and F. J. Dixon. 1975. Failure of heparin to affect two types of experimental glomerulonephritis in rabbits. Kidney Int. 8:140–148.
32. Tipping, P. G., and S. R. Holdsworth. 1986. The participation of macrophages, glomerular procoagulant activity and Factor VIII in glomerular fibrin deposition: Studies in anti-glomerular base membrane antibody induced glomerulonephritis in rabbits. Am J Pathol. 124:10–17.
33. Tipping P. G., Worthington L. A., and Holdsworth S. R. 1987. Quantitation and characterisation of glomerular procoagulant activity in experimental glomerulonephritis. Lab Invest 56:155–159.
34. Yamabe, H., H. Osawa, H. Inuma, M. Kaizuka, N. Tamura, S. Tsunoda, Y. Fujita, K. Shirato, and K. Onodera. 1995. Tissue factor pathway inhibitor production by human mesangial cells in culture. J Am Soc Nephrol. 6:916 (Abstract).

What is claimed is:

1. A method of inhibiting fibrin-dependent glomerulonephritis in a warm-blooded mammal in need thereof as being vulnerable to glomerulonephritis caused by glomerular fibrin deposition comprising administering to said mammal a pre-formed heparin/TFPI complex consisting of a weight ratio of at least 1.25 parts of heparin to one part of TFPI.

2. The method of claim 1 in which the weight ratio is from 1.25 to about 100 parts of heparin to one part of TFPI.

3. The method of claim 1 in which the heparin/TFPI complex is administered intravenously from solution in physiologically acceptable buffer.

4. The method of claim 2 in which the heparin/TFPI complex is administered intravenously from solution in physiologically acceptable buffer.

5. The method of claims 1, 2, 3 or 4 in which the TFPI is full-length TFPI.

* * * * *